Figure 1:
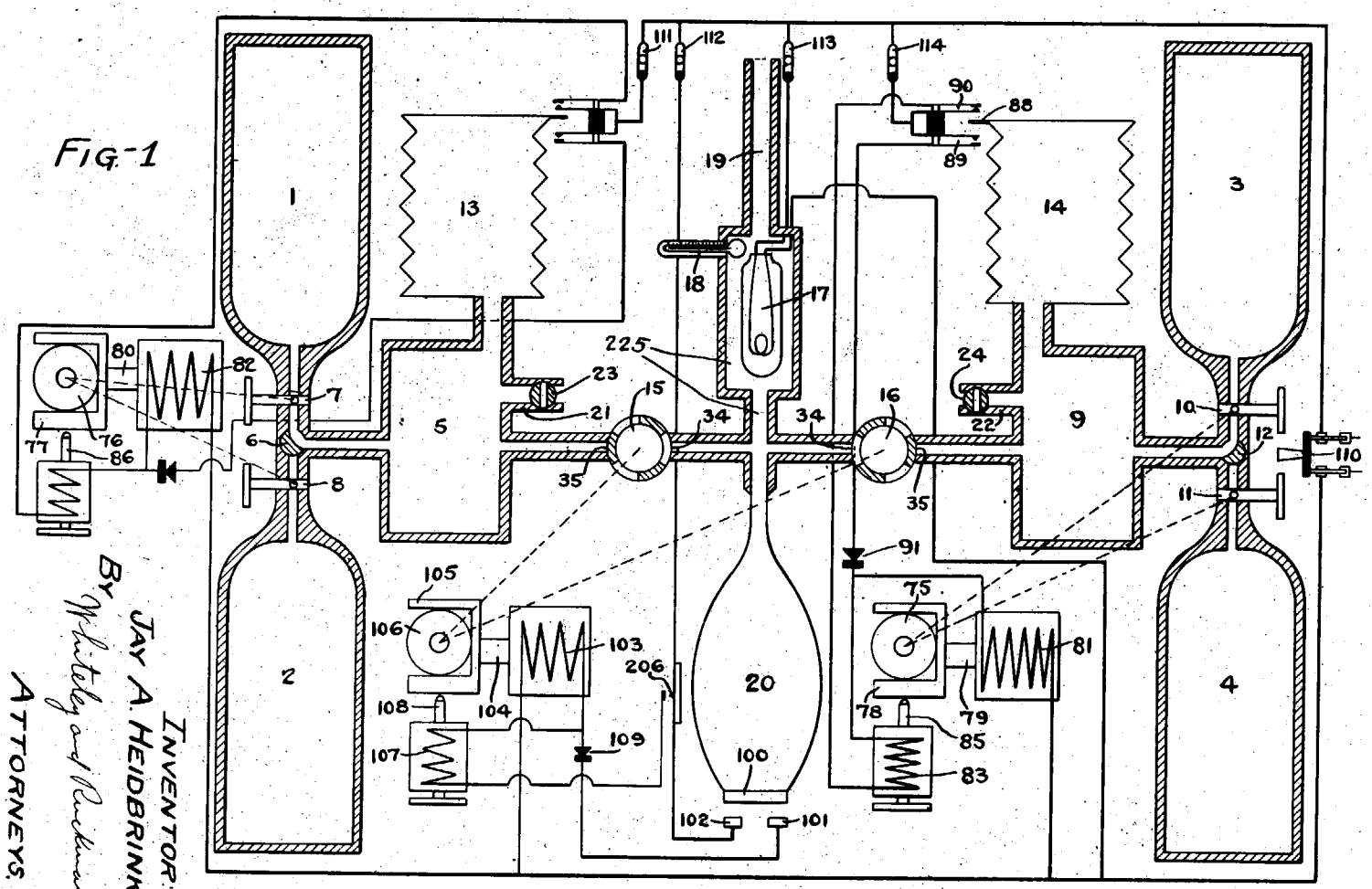

July 22, 1924.

Re. 15,873

J. A. HEIDBRINK

ANÆSTHETIC APPARATUS

Original Filed Nov. 23, 1911 5 Sheets-Sheet 1

INVENTOR:
JAY A. HEIDBRINK
BY Whiteley and Ruckman
ATTORNEYS.

July 22, 1924. Re. 15,873
J. A. HEIDBRINK
ANÆSTHETIC APPARATUS
Original Filed Nov. 23, 1911 5 Sheets-Sheet 2
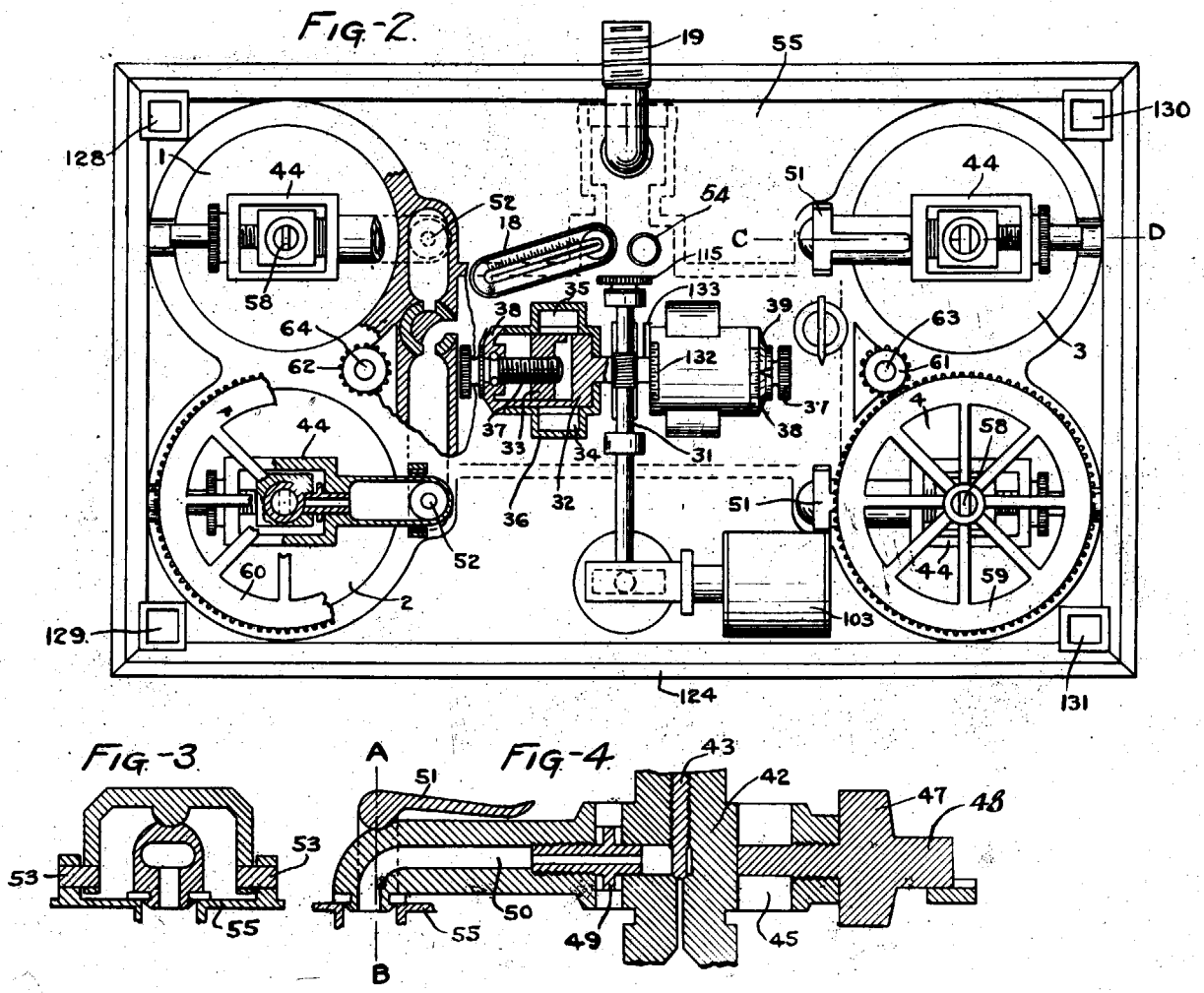
INVENTOR:
JAY A. HEIDBRINK
BY Whiteley and Ruckman
ATTORNEYS.

July 22, 1924. Re. 15,873

J. A. HEIDBRINK

ANÆSTHETIC APPARATUS

Original Filed Nov. 23, 1911 5 Sheets-Sheet 3

INVENTOR:
JAY A. HEIDBRINK
BY Whiteley and Ruckman
ATTORNEYS.

July 22, 1924. Re. 15,873

J. A. HEIDBRINK

ANÆSTHETIC APPARATUS

Original Filed Nov. 23, 1911 5 Sheets-Sheet 4

INVENTOR:
JAY A. HEIDBRINK
BY Whiteley and Ruckman
ATTORNEYS.

July 22, 1924. Re. 15,873
J. A. HEIDBRINK
ANÆSTHETIC APPARATUS
Original Filed Nov. 23, 1911 5 Sheets-Sheet 5
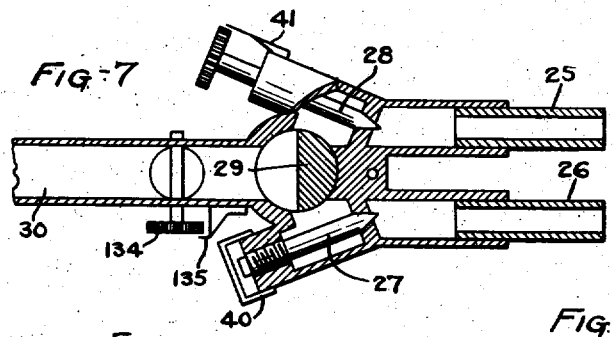
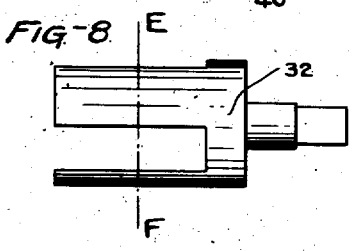
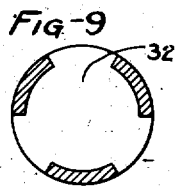
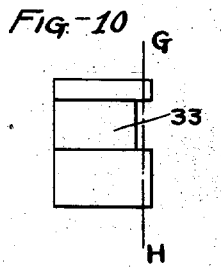
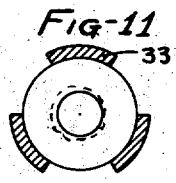
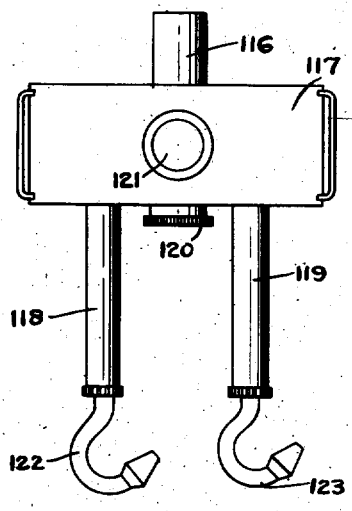
FIG-12
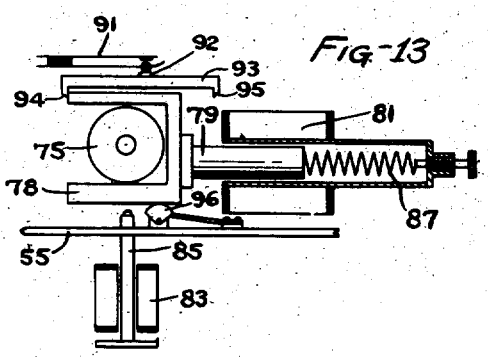
INVENTOR:
JAY A. HEIDBRINK.
BY Whiteley and Rickman
ATTORNEYS.

Reissued July 22, 1924. Re. 15,873

UNITED STATES PATENT OFFICE.

JAY A. HEIDBRINK, OF MINNEAPOLIS, MINNESOTA.

ANÆSTHETIC APPARATUS.

Original No. 1,309,686, dated July 15, 1919, Serial No. 662,066, filed November 23, 1911. Application for reissue filed May 2, 1924. Serial No. 710,661.

*To all whom it may concern:*

Be it known that I, JAY A. HEIDBRINK, a citizen of the United States, and a resident of Minneapolis, in the county of Hennepin and State of Minnesota, have invented certain new and useful Improvements in Anæsthetic Apparatus, of which the following is a specification.

My invention relates to apparatus for producing a state of anesthesia by the inhalation of a mixture of nitrous-oxid ($N_2O$) and oxygen (O). With the proper mixture of these two gases anesthesia may be produced and maintained for a length of time sufficient to perform the most delicate and difficult surgical or dental operation with a minimum of nausea or other bad effects resulting and with no danger to the life of the subject.

The vital point in this method is to secure a constant and uniform flow of each of the gases so as to provide a mixture having a predetermined proportion of the gases and which mixture will at all times be uniform while the same is being delivered and administered to the patient. It is the object of this invention to provide a reliable apparatus which will so uniformly deliver a mixture of the gases in a fixed proportion thereof or in exactly predetermined relation. Other objects of the invention are to change the proportions or quantitative relations of the gases in the mixture delivered at will, to indicate the proportions at all times, to electrically warm the gases and indicate the temperature of the mixture delivered and to provide details of construction for carrying out these objects.

A particular means of effecting the particular objects of the invention consists in providing separate and independent connections or passageways from the respective sources of supply of oxygen and of nitrous oxid with the mixing chamber by means of separate passageways each having a valve at one end adjacent the gas container and at the other end adjacent the mixing chamber, and of providing intermediate of these valves a flexible expansion chamber constituting a reservoir for a relatively large volume of gas at a relatively low pressure from which the gas is fed through the exit valves into the mixing chamber, and further to provide means for operating the flow or admission valve which has a connection with the movable wall of the expansible reservoir for causing the operation of the inlet valves to admit and shut off admission of gas to the respective passageways and reservoirs.

To enable those skilled in the art to which my invention relates to more fully understand the construction, operation and advantages thereof, a particular embodiment is more fully set forth in the following specification and illustrated in the accompanying drawings in which like figures of reference indicate similar parts throughout the several views.

In the drawing—

Figure 5:
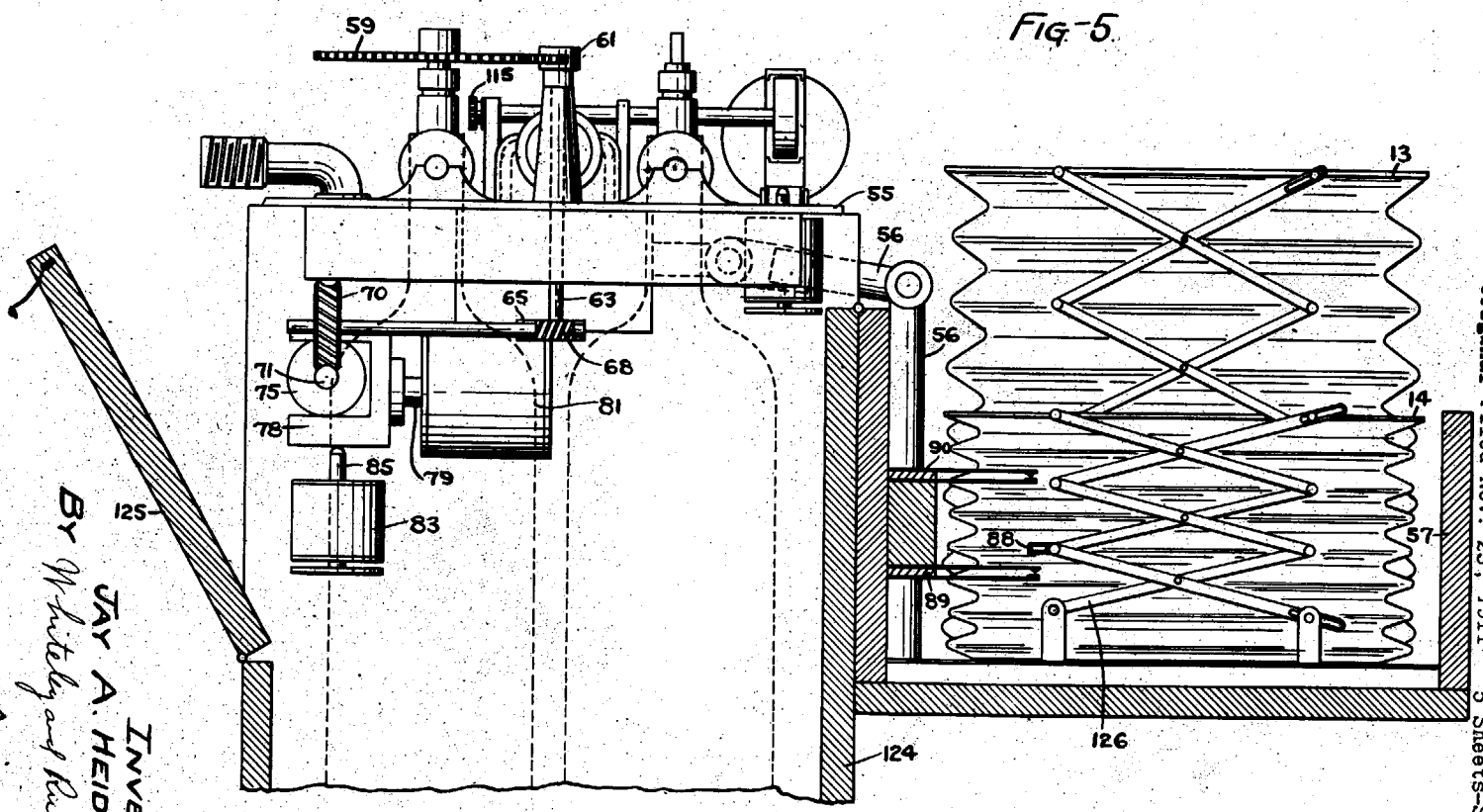
Figure 6:
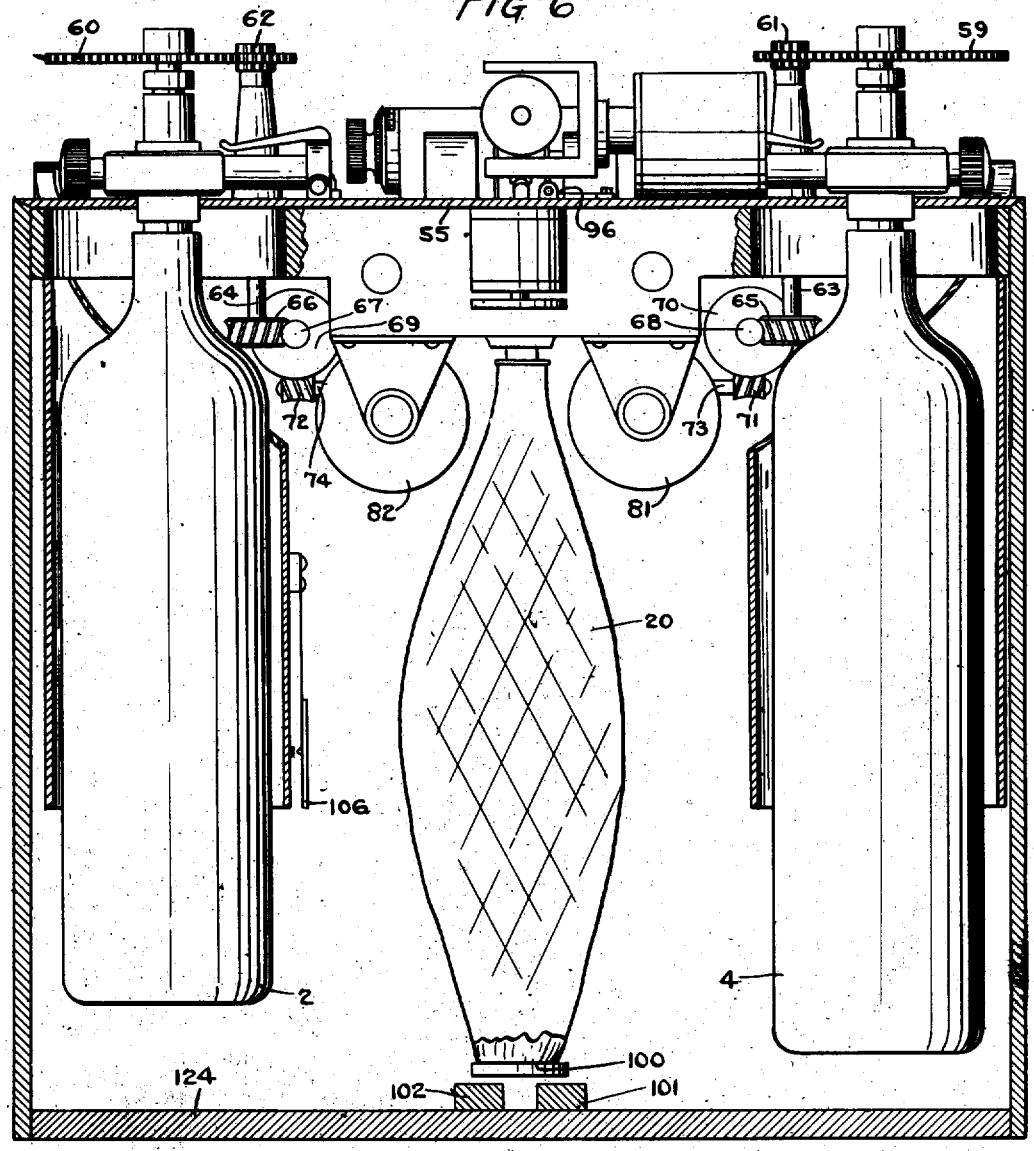

Figure 1 is a diagrammatic view of my apparatus showing the pipes, wiring, etc. Fig. 2 is a top plan view of my apparatus with the cover removed, parts being broken away and parts in horizontal section. Fig. 3 is an enlarged vertical section on the line A—B, Fig. 4. Fig. 4 is an enlarged vertical section on one of the clamping attachments and a part of one of the gas cylinder valves taken on the line C—D, Fig. 2. Fig. 5 is a partly broken away, partly sectional end view showing the door on the front of the case partly open and the case cover open containing the bellows partly inflated, parts also being shown in dotted lines for the sake of clearness. Fig. 6 is a side elevation partly in section and partly broken away. Fig. 7 is a partly sectional and partly broken away view of the mouth inhaler. Fig. 8 is an enlarged elevation of a part of one of the total flow or proportioning valves and will be explained further on. Fig. 9 is a section on the line E—F in Fig. 8. Fig. 10 is an enlarged elevation of another part of one of the proportioning valves. Fig. 11 is a section on the line G—H in Fig. 10. Fig. 12 is an elevation of a nasal inhaler. Fig. 13 is a diagrammatic view of one of the electrical valve operating mechanisms.

As shown in Fig. 1, two gas cylinders containing compressed nitrous oxid are connected to the passageway embodying the chamber 5 in communication with the expansible member 13, and, similarly, at opposite sides of the apparatus cylinders 3, 4 containing pure oxygen, are connected with a passageway including a chamber 9 in connection with the expansible member 14. Small regulating valves of any desired and known type may be employed to control the flow of gas from the respective cylinders 1, 2 and 3, 4, and three-way cocks 6 and 12 cut out one of each set of cylinders. A small pointer on each three-way valve indicates the cylinder being used. My invention, however, does not require more than one nitrous oxid cylinder, as 1, and one oxygen cylinder, as 3, from each of which a continuous passageway is shown extending to the valve members 15 and 16 which admit the gas to the warming and mixing chamber 225. The regulating valves for the cylinders 1, 2 are indicated by numerals 7, 8 and for the cylinders 3, 4 by the numerals 10, 11; and the expansible members 13, 14 are in the form of bellows devices which are identical in construction and are designed to maintain equal pressure in the passageways and chambers 5, 9, and each to provide a reservoir for a relatively large volume of gas at a relatively low pressure from which said gas is delivered through the passageways to the mixing chamber. As shown, having reference to Figs. 5 and 6, the bellows are relatively large containers while the chambers 5 and 9 are in the form of expansions of the passageways leading from the supply sources to the proportioning valves 15, 16 and through these valves into the mixing chamber 225 around the warming lamp 17 and the thermometer 18 to the main discharge pipe 19. From this main discharge pipe a hose, not shown, conducts the mixture to the inhaler attached to the subject and comprises the gas administering passageway of the apparatus.

A gas bag 20 is provided to hold a sufficient quantity of the mixture to enable the subject to breathe regularly and easily at all times and also to relieve any excessive pressure that might pass the proportioning valves 15, 16, it being desirable to have the mixture at such a slight pressure that it will only flow through the discharge pipe 19, when the subject being anesthetized inhales.

Two pipes 21, 22, together with their cut-off valves 23, 24, connect with the expansion chambers 5, 9. Tubes, not shown, connecting with these pipes 21, 22, pass to the mouth inhaler shown in Fig. 7, where they connect with the two pipes 25, 26, leading through the regulating valves 27, 28, and the cut-off valve 29, to the mouth discharge pipe 30, one end of which is placed in the open mouth of the subject. This mouth inhaler is especially designed for operations in the mouth and head when it is necessary to keep the subject's mouth open during the operation as in dental work. The subject may be anesthetized with a nasal inhaler even though the mouth be open, the subject's self control causing nasal breathing even in a prolonged state of analgesia; however when a complete state of anesthesia has been produced the subject is liable to breathe through the mouth and provision is thus made to keep the mouth filled at all times with the proper mixture of anesthetizing gases in order to prevent the subject's breathing a sufficient amount of air to counteract the anæsthetic.

The regulating valves 27, 28, in the mouth inhaler serve to regulate the quantitative mixture of the gases since they are taken from the expansion chambers 5, 9, and do not pass through the main mixing valves 15, 16. In this instance the gases are taken directly from the expansion chambers in order to get a sufficient pressure to cause them to flow into and fill the mouth of the subject at all times.

If one of the cylinders 1, 2, containing nitrous-oxid should become exhausted during an operation, the three-way valve 6, may be turned to instantly place the other cylinder in operation. The three-way valve 12, may be used to change the oxygen cylinders in the same manner.

The two total flow valves 15, 16, which are also the main proportioning valves, are controlled by a common shaft 31 (Fig. 2), and operate together as one valve. Each of these valves 15, 16, is made up of two main parts 32, 33, which are cylindrical in shape each having three equal slots and three extensions. These parts are shown in detail in Figs. 8 to 11. Each of the three extensions around the periphery of the two parts 32, 33, fits snugly into the slots in the other part and when put together form a closed hollow cylindrical valve which entirely closes both of the ports 34, 35 in the valve chamber 36 (Fig. 2). A regulating screw 37, passing through the valve chamber head 38, engages with its threaded portion the threaded center opening of the part 33 of the valve which is thereby longitudinally movable in the chamber 36. It will thus be seen that when the screw 37 is turned the valve part 33 will be withdrawn sligthly from the valve part 32, leaving three open ports around the periphery of the valve as shown best in Fig. 1. Each of these ports will extend around one-sixth of the circumference of the valve, or sixty degrees. The width of these ports depends upon the amount the screw 37 is turned, its pitch, etc. By turning the shaft 31 together with the valve parts two of these openings will be brought opposite the two ports 34, 35 in the valve case, thus permitting the gas to flow through the valve.

The proportion of the respective gases in the mixture is governed by the distance the valve parts 32, 33 are apart while the total flow is governed by the distance the valve is turned in the port openings 34, 35, and indicated on the scale 132 by the pointer 133 attached to the common shaft 31. The port openings are in the form of the lateral areas of segments of cylinders. The distance apart of the sets of valve parts 32, 33, respectively for the oxygen and the nitrous oxid, determines the respective widths of the segmental cylindrical areas and in that way fixes the proportion of gases going to the mixing chamber. If it is desired to deliver a mixture of ten parts of nitrous-oxid to one part of oxygen the opening between the valve parts 32, 33 of the nitrous-oxid valve 15 is made ten times as large as the opening between the valve parts of the oxygen valve 16, that is, the cylindrical segment for nitrous oxid delivery will be ten times as wide as and have ten times the area of the cylindrical segment for oxygen delivery. Both valve members 15 and 16 are turned by the common shaft 31, which has the effect of increasing in the same amounts the lengths or circumferential extent of the segmental cylindrical delivery openings for the nitrous oxid and the oxygen respectively.

The valve chamber head 38 is integrally connected to the valve part 32, and shaft 31, and revolves therewith. A small indicator point on the screw 37 shows at all times by means of a scale 39 on the valve chamber head 38, the proportionate amounts of opening of the ports of the valves, and since the two gases are at the same pressure this will give the exact mixture delivered.

Although two of these adjusting screws 37 are shown (one for each valve 15, 16), only one will in practice need to be used. The nitrous-oxid valve will be fixed at a certain opening (i. e. a certain distance between the valve parts), the scale and indicator point of the oxygen valve indicating the percentage of oxygen in the total mixture delivered.

In order to determine the proportions of the gases in the mixture delivered by the mouth inhaler the short screw valve 27 is opened a certain amount and a cap 40 placed over it to prevent its being tampered with. The percentage of oxygen in the mixture is then regulated by the hand valve 28 and indicated by the pointer 41. A butterfly valve 134 in the mouth pipe 30 serves to regulate the amount of mixture delivered, the amount being indicated by a pointer 135.

Nitrous-oxid and oxygen may be purchased on the open market compressed in cylinders 1, 2, 3, 4, as shown. These cylinders have a standard square neck 42 (Fig. 4), and are provided with a needle valve 43 which may be operated by a small hand or gear wheel. As it is of the utmost importance to keep a constant supply of both nitrous-oxid and oxygen during a prolonged operation it is advisable to have several extra cylinders on hand to replace any that may be emptied. As my apparatus is provided with means for holding two of each of the cylinders, when one of either kind is discharged totally the other may be turned on and used while the discharged cylinder is being replaced by a full one.

Clamping attachments 44, 44 (Fig. 2) are provided for each of the cylinders in use in the apparatus and extra clamps are provided for all extra cylinders on hand. This clamping attachment comprises a frame or yoke 45 (Fig. 4), which goes around the square neck 42 of the cylinder; a clamping screw 47, with an extension 48 at its outer end to support a part of the weight of the cylinder when in use; a nipple 49 extending into the opening in the square neck 42 of the cylinder; and a curved hollow neck 50 extending outward from the nipple 49, and adapted to be quickly clamped in place on the apparatus by means of a clamp 51, one of which is located over one of each of the discharge openings 52, 52, in the machine proper. Gaskets of rubber or some similar material are provided to make tight joints around the nipple 49, and the outer end of the curved neck 50. Thus the clamp 51 may be quickly raised, the drum and clamping attachment lifted out, and another drum or cylinder and clamping attachment clamped in position in a very short time. The clamp 51 is swiveled on its bearings 53, 53, as shown in Fig. 3.

The gases on expanding produce a low temperature and in case of a long period of anesthesia would irritate the subject's air passages if means were not provided for warming the mixture before it passes the inhaler. For this purpose an incandescent electric light 17 is placed in such a position that the mixture must pass over and around it, and in so doing absorb sufficient heat from the light bulb to warm the gases to a normal temperature. A small opening 54 (Fig. 2) is made in the top covering plate 55 of the apparatus directly over a portion of the light bulb and provided with a glass closure to enable the operator to know at all times that the light is burning.

A small thermometer 18, with its bulb interposed in the warming chamber, is always in plain view of the operator showing at all times the exact temperature of the mixture as it passes to the inhaler.

It is very evident that in order to obtain a mixture of predetermined proportions of the respective gases by means of the relative sizes of openings in the main valves 15, 16, the pressure of the nitrous-oxid in the expansion chamber 5 must always be exactly equal to the pressure of the oxygen in the expansion chamber 9. In order to maintain equal pressure in these two chambers 5, 9, the two identical bellows members 13, 14 are provided and are always connected directly to the chambers 5, 9 by hinged telescoping pipes, one of which, 56, is shown in Fig. 5 partly in dotted lines. The only object of the hinges and telescoping arrangement is to provide means for carrying the gases into the hinged lid where the bellows are located. These bellows are guided in their movements by light lazy-tongs devices 126, 127, and may carry weights to give variations of pressure to the contents as desired.

In order to maintain a normal amount of the gases in the bellows at all times an automatic control is arranged to govern the flow of the gases through the valves 7, 8, 10, 11. These valves, designated 43 and shown more plainly in Fig. 4, have a large stem extending upward. These stems 58, 58, (Fig. 2) are adapted to be engaged by hand or gear wheels 59, 60, which in turn are engaged by small pinions 61, 62 integrally mounted on the upper ends of small shafts 63, 64. These pinions are so arranged as to engage the wheels 59, 60, when placed in position to operate either one of the two cylinders at each end of the apparatus. Thus, if the three-way valve 6 were turned to discharge from the cylinder 1, the wheel 60 would then be placed on the valve stem 58 of the same cylinder 1. On the lower ends of the pinion shafts 63, 64 (Fig. 6), are worm wheels 65, 66 which are engaged by worms 67, 68 mounted integrally to rotate with other worm wheels 69, 70. These worm wheels 69, 70, are engaged by worms 71, 72, which are integrally mounted on shafts 73, 74, on the opposite ends of which are mounted friction wheels 75, 76, one of which 75, mounted on the shaft 73, with the worm 71, is shown in Fig. 5.

These friction wheels 75, 76, are operated by the yokes 77, 78, and the armatures 79, 80, 85, 86, as is shown more plainly in Figs. 1 and 13. The coil spring 87 pushing against the armature 79 keeps it normally at its outer limit of travel as shown in the drawing. When the bellows 14 is partially exhausted the stop 88 (Figs. 1 and 5) comes in contact with the upper contact spring of the switch 89, pressing it against the lower contact spring and closing the electrical circuit through the solenoid 81, thus drawing in the armature 79 and yoke 78.

The weight of the heavy yoke 78 resting upon the upper part of the friction wheel 75 causes it to revolve a part of a revolution and thus operating the train of worm wheels and gears to turn the pinion 61 and thus open one of the valves 10, 11, in the cylinder necks according to which cylinder is in use.

Another switch 91, located near the yoke 78, is interposed in circuit with the solenoid 81 and operated by a small projection 92 on the slide 93. This slide 93 is operated by the yoke 78 striking upon small projections 94, 95, at either end of the slide 93.

As the armature is drawn in to its inner limit of travel the yoke 78, striking the projection 95, on the slide 93, moves it to the right. The projection 92, on the slide 93, being thus withdrawn from contact with the lower spring of the switch 91, the springs of this switch are permitted to come apart and open the solenoid circuit. The armature 79 is thus released and the coiled spring 87, which has been compressed by the indrawn armature, now pushes the armature out again to its normal position. As the armature 79 is pushed out by the spring 87 the outer end of the yoke 78, striking against the projection 94, moves the slide 93 back to its normal position, causing the contacts of the switch 91 to again close the circuit operating the solenoid 81 and thus to repeat the cycle of operations until the oxygen liberated by the opening of one of the valves 10, 11, in the cylinder necks raises the bellows 14, with its stop 88, high enough to release the upper spring of the switch 89 and open the solenoid circuit and stop the action of the armature 79. It should be noted in the operation of the armature 79, and yoke 78, that as the spring 87 pushes the armature to its outward position, the small cam 96, operating by friction due to the weight of the yoke, turns from the position shown in Fig. 13 to that shown in Fig. 6, thus raising the yoke high enough that its upper arm does not rest upon the friction wheel 75, yet not so high that its lower arm comes in contact with the under side of the wheel 75. In his way no impulse is given the wheel on the outward stroke of the armature. The cam 96 is assisted by a leaf spring engageable beneath a portion thereof in its lifting movement, said spring being compressed by the turning of the eccentric through friction of the arm 78 upon the same when said arm is moved under the influence of solenoid 81.

When the bellows 14 is nearly filled with oxygen the stop 88, coming in contact with the lower spring of the switch 90, causes it to come in contact with the upper contact spring and thus close the double solenoid circuit as is plainly shown in Fig. 1, operating the lower solenoid 83 at the same time the upper solenoid 81 is operated. The armature 85 of the lower solenoid 83 carries a small roller at its upper end which is pressed against the underside of the yoke 78, when both solenoids are operated and raising the yoke until its lower arm presses against the underside of the friction wheel 75, thus causes the friction wheel to be turned in an opposite direction to that in which it turns when only the upper solenoid 81 is operated.

The two solenoids operate together in this manner until the oxygen is turned off enough to permit the bellows 14 to lower and release the switch contacts 90, which, coming apart, open the circuit and thus stop the action.

The bellows 13 regulates the flow of nitrous-oxid from the cylinders 1, 2, in the same manner by means of its solenoids 82, 84, armatures 80, 86, yoke 77, friction wheel 76, and worm gear train to the valves 7, 8, and the switches 97, 98, 99, corresponding to the switches 89, 90, 91, of the oxygen side.

After the gases have passed the proportioning valves 15, 16, they are at liberty to fully expand by flowing freely into the light suspended bag 20 and thus practically all pressure is relieved, the bag 20 also acting as a reservoir to supply the intermittent breathing of the subject. To the lower part of this supply bag 20 is attached a light metal plate 100, which, when the bag is almost empty, rests upon the two switch contacts 101, 102, and bridging across between them closes the circuit through the solenoid 103 which operates its armature 104 and yoke 105 and friction wheel 106, together with a suitable worm gear train to open the total flow or main mixing valves 15, 16, in the same manner that the solenoids 81, 82, open the nitrous-oxid and oxygen valves 7, 8, 10, 11.

The switch thus closed by the plate 100 corresponds in its action in its circuit to the switches 89 and 98 in their respective circuits already described. When the bag 20 is filled it presses lightly against the switch 206, shown plainly in Fig. 6, and closing it causes the solenoids 103, 107, to be operated together in the manner already described in the operation of the oxygen regulating solenoids 81, 83, and thus slowly close the mixing valves 15, 16, until the bag 20, becoming partly exhausted, releases the switch 206. The switch 109 in its functions corresponds to the switches 91 and 99 in their functions.

Thus, the quality of mixture going to the patient is automatically kept uniform and the rate of the flow of the mixture is automatically determined and neither of these functions of the machine requires any of the operator's attention. The proportioning valves being set to determine the rate of flow of the respective gases into the mixing chamber and the mixture bag 20, the respective gases will be caused to continue to flow in these proportions from the reservoirs formed by the expansible bellows members, which flow will always be constant because as gas is taken from these reservoirs it will constantly be replenished by the automatic operation of the delivery valves effected by the volume of gas in the expansive members or reservoirs. In turn the delivery of this constant mixture to meet the needs of the patient will be determined by the volume of gas in or taken from the mixture container 20.

The electrical current may be derived from any convenient source and is admitted to the apparatus by a double pole switch 110, and may be entirely disconnected by opening the switch 110. The solenoid set circuits and also the lamp circuits are controlled by individual single pole switches 111, 112, 113, 114, by means of which any solenoid set or the lamp may be turned off at will.

The cylinder valves, 7, 8, 10, 11, may be operated by hand by raising the gear wheels 59, 60, out of engagement with the small pinions 61, 62. In the same manner the main valves 15, 16, may be operated by means of the thumb nut 115 (Fig. 5), mounted on the same shaft with the friction wheel 106. Any desired form of inhaler may be used, a nasal inhaler being shown in Fig. 12. This inhaler is attached to the subject's forehead and a hose from the main discharge pipe 19 on the machine proper to the intake pipe 116 on the inhaler. The mixture passing through the intake pipe 116 enters the chamber 117 which is provided with two flexible outlet pipes 118, 119, an air valve 120 and an exhaust valve 121. These flexible outlet pipes 118, 119, are provided with curved nostril pieces 122, 123, which are swivel connected to the flexible outlet pipes in such a manner as to be fitted snugly to the subject's nostrils.

The entire apparatus is inclosed in a carrying case 124 provided with a deep hinged cover 57 in which are located the bellows 13, 14, in such a manner that they may be folded into the cover when it is closed. Four telescoping legs 128, 129, 130, 131 (Fig. 2) are provided at the corners of the case 124 which slide up into the case when not in use. A door 125 on the front of the case 124 may be opened when the apparatus is in operation so that all operating parts will always be in full view of the operator.

I claim:

1. An anæsthetic administering apparatus comprising means including delivery valves for producing a mixture of gases of a predetermined proportion, an expansible member for receiving the mixture as the same is delivered from the valves, and a system of solenoids controlled by movement of said expansible member for controlling the valves.

2. A gas administering machine comprising a plurality of sources of fluid supply under pressure, a mixing chamber, a passageway leading from each of said sources of supply to the mixing chamber for conducting each of said gases separately into the mixing chamber, a valve in each of said passageways for admitting gas from its respective source thereinto, two flexible expansion members each having separate connection with one of said passageways and constituting a reservoir for a relatively large volume of gas at a relatively low pressure for delivery therefrom through said passageway to the mixing chamber, and means caused to operate by the movement in expansion and contraction of said flexible members for opening and closing said valves to admit and shut off flow of gas into said reservoirs.

3. A gas administering machine comprising a source of oxygen supply and a source of nitrous oxid supply each under pressure, a mixing chamber, a passageway leading from said oxygen supply and a separate passageway leading from said nitrous oxid supply to the mixing chamber for conducting each of said gases separately into the mixing chamber, valve mechanism at the entrance to the mixing chamber for regulating the amount of oxygen and the amount of nitrous oxid entering said mixing chamber from the respective passageways so as to produce a mixture thereof in predetermined proportions, a valve in each of said passageways for admitting oxygen and nitrous oxid respectively into its passageway, a flexible expansion member having connection with the oxygen passageway, and a flexible expansion member having connection with the nitrous oxid passageway, each of said members constituting a reservoir for a relatively large volume of gas at a relatively low pressure for delivery therefrom through its passageway to the mixing chamber, and means caused to operate by the movement in expansion and contraction of said flexible member for opening and closing said valves to admit and shut off the flow of gas into said reservoirs.

4. A gas administering machine comprising a plurality of gas supplies each separately connected to a supply line, an expansion chamber in each of said connections, valves in each of said connections, a flexible expansion member in each of said connections adapted to be inflated and deflated by the introduction and withdrawal of gas therefrom, and means operative from said expansion members for operating said valves to cause them to admit and cut off delivery of gas to the expansion members.

5. A gas administering machine comprising an oxygen container and a nitrous oxid container, valves for each of said containers, expansible gas reservoirs each having connection with one of said valves, and means operative from the expansion of said reservoirs for operating said valves to cause them to deliver a variable flow of oxygen and nitrous oxid to the respective reservoirs, and means controlling the delivery of said gases at reduced pressure and in a constant proportion from said reservoirs.

6. In a device of the class described, a series of fluid containers, valves and flexible expansion chambers having connection with said containers, means operative from the expansion of said chambers for operating said valves to provide a mixture of the gases, means controlling the flow of the respective gases to vary the proportion thereof, and an indicator for indicating the proportion.

7. In anæsthetic apparatus arranged to be equipped with a compressed gas cylinder, a regulating valve in communication with the gas supply from such cylinder, an expansible elastic gas bag constituting a variable-pressure reservoir for a relatively large volume of gas at a relatively low pressure in free communication with the gas administering passages of the apparatus, and means governed by the inflation of such bag for controlling said regulating valve.

8. A gas administering machine comprising a compressed gas cylinder, a regulating valve in communication with the gas supply from such cylinder, an expansible elastic gas bag constituting a reservoir for a relatively large volume of gas at a relatively low pressure, a gas administering passage having communication with said reservoir, means governed by the inflation and deflation of the reservoir for controlling the regulating valve to admit or cut off gas from the said reservoir, and means for carrying the pressure imposed upon the gas by and in said reservoir.

9. A gas administering machine comprising a pair of compressed gas cylinders one containing oxygen and the other nitrous oxid, a regulating valve in communication with the gas supply from each cylinder, an expansible elastic gas bag having connection with each cylinder and constituting a reservoir for a relatively large volume of gas at a relatively low pressure, a gas administering passage having separate communication with each reservoir, separate means governed by inflation and deflation of each reservoir for controlling the respective regulating valves to admit or cut off gas from said reservoirs, and means for varying the pressure imposed upon the gas by and in each reservoir.

10. A gas administering machine comprising a plurality of gas supplies each separately connected to a mixing chamber and patient's supply line, valves in each of said connections, a flexible expansion member in each of said connections adapted to be inflated and deflated by the introduction and withdrawal of gas therefrom, and means connected with each of said valves and caused to operate by reason of movements of the walls of one of said expansion members for operating said valves to cause them to admit and cut off delivery of gas to the respective expansion members.

11. A gas administering machine comprising a pair of compressed gas cylinders, one containing oxygen and the other nitrous oxid, a mixing chamber, an independent passageway for conducting each of said gases to the mixing chamber, a regulating valve in each of said passageways adjacent the gas cylinder, other valve mechanism at the ends of said passageways for determining the relative rate of flow of the respective gases into the mixing chamber, a flexible expansion member connected in each of said passageways intermediate said valves and each of said members constituting a reservoir for a relatively large volume of gas at a relatively low pressure, a flexible expansion member connected to the mixing chamber for receiving mixture therefrom and constituting a reservoir for a relatively large volume of said mixture, separate means governed by the inflation and deflation of each of the reservoirs first named for controlling the respective regulating valves to admit or cut off gas from said reservoirs, and means governed by the inflation and deflation of said mixture reservoir for controlling the mixing chamber valve mechanism to admit or cut off flow of both gases into the mixing chamber and to admit or cut off flow of mixture from said mixing chamber into the mixing reservoir.

In testimony whereof I have hereunto affixed my signature.

JAY A. HEIDBRINK.